(12) United States Patent
Dobschal

(10) Patent No.: US 9,690,882 B2
(45) Date of Patent: Jun. 27, 2017

(54) LENS HAVING AN EXTENDED RANGE OF FOCUS AND METHOD OF MAKING THE SAME

(71) Applicant: Carl Zeiss AG, Oberkochen (DE)

(72) Inventor: Hans-Juergen Dobschal, Kleinromstedt (DE)

(73) Assignee: Carl Zeiss AG, Oberkochen (DE)

( * ) Notice: Subject to any disclaimer, the term of this patent is extended or adjusted under 35 U.S.C. 154(b) by 323 days.

(21) Appl. No.: 14/227,748

(22) Filed: Mar. 27, 2014

(65) Prior Publication Data
US 2014/0211313 A1    Jul. 31, 2014

Related U.S. Application Data

(63) Continuation of application No. PCT/EP2012/004026, filed on Sep. 26, 2012.

(30) Foreign Application Priority Data

Sep. 29, 2011  (DE) .......................... 10 2011 114 752

(51) Int. Cl.
*G06F 17/50* (2006.01)
*G02B 5/30* (2006.01)
(Continued)

(52) U.S. Cl.
CPC .......... *G06F 17/50* (2013.01); *A61F 2/1618* (2013.01); *A61F 2/1654* (2013.01); *G02B 3/00* (2013.01);
(Continued)

(58) Field of Classification Search
CPC ........ A61F 2/16; A61F 2/1613; A61F 2/1616; A61F 2/1618; A61F 2/1621;
(Continued)

(56) References Cited

U.S. PATENT DOCUMENTS

| 4,986,939 A | 1/1991 | Hoffmann |
| 5,408,281 A | 4/1995 | Zhang |

(Continued)

FOREIGN PATENT DOCUMENTS

| DE | 10 2009 033 984 A1 | 2/2011 |
| DE | 10 2011 101 899 A1 | 11/2012 |

(Continued)

OTHER PUBLICATIONS

English translation of the Office action of the Japanese Patent Office dated Dec. 10, 2015 in corresponding Japanese patent application 2014-532273.

(Continued)

*Primary Examiner* — Bumsuk Won
*Assistant Examiner* — Ephrem Mebrahtu
(74) *Attorney, Agent, or Firm* — Walter Ottesen, P.A.

(57) ABSTRACT

A lens having an extended range of focus is made of a transparent material and has two optical surfaces. The lens defines an optical axis and a focal power distribution ($F_{tot}$) which, in relation to a plane perpendicular to the optical axis, changes as a function of the radial height (r) and of the azimuth angle (phi) of the aperture between a calculated basic value of the focal power ($F_{lens}$) not equal to zero and a maximum value $F_{spiral\ max}$(r, phi).

15 Claims, 7 Drawing Sheets

(51) Int. Cl.
*G02B 3/00* (2006.01)
*G02B 27/00* (2006.01)
*G02B 5/18* (2006.01)
*G02C 7/06* (2006.01)
*A61F 2/16* (2006.01)
*G02C 7/02* (2006.01)

(52) U.S. Cl.
CPC ......... *G02B 5/1823* (2013.01); *G02B 5/1842* (2013.01); *G02B 5/1871* (2013.01); *G02B 5/30* (2013.01); *G02B 27/0075* (2013.01); *G02C 7/061* (2013.01); *G02C 7/022* (2013.01); *G02C 2202/20* (2013.01)

(58) Field of Classification Search
CPC ...... A61F 2/1624; A61F 2/164; A61F 2/1643; A61F 2/1648; A61F 2/1651; A61F 2/1654; A61F 2/1656; G02C 7/022; G02C 7/024; G02C 7/04; G02C 7/041; G02C 7/042; G02C 7/043; G02C 7/044; G02C 7/045; G02C 7/06; G02C 7/08; G02C 2202/18; G02C 2202/20; G02C 7/028; A61L 2430/16; G06F 17/50; G02B 3/00
USPC ............ 351/159.05, 159.41–159.48, 159.74; 623/6.11, 6.23–6.37; 359/569
See application file for complete search history.

(56) References Cited

U.S. PATENT DOCUMENTS

| | | |
|---|---|---|
| 5,982,543 A | 11/1999 | Fiala |
| 6,120,148 A | 9/2000 | Fiala et al. |
| 6,330,118 B1 | 12/2001 | Daschner et al. |
| 6,536,899 B1 | 3/2003 | Fiala |
| 6,822,794 B2 | 11/2004 | Coleman et al. |
| 6,856,460 B2 | 2/2005 | Coleman et al. |
| 8,335,034 B2 | 12/2012 | Bernet et al. |
| 2001/0036018 A1 | 11/2001 | Arai |
| 2006/0176572 A1 | 8/2006 | Fiala |
| 2009/0122150 A1 | 5/2009 | Shabtay et al. |
| 2010/0002310 A1 | 1/2010 | George et al. |
| 2010/0329605 A1* | 12/2010 | Graham ............... G02B 6/4207 385/33 |
| 2011/0279912 A1 | 11/2011 | Fiala |
| 2013/0138208 A1* | 5/2013 | Simonov ............... A61F 2/1624 623/6.11 |

FOREIGN PATENT DOCUMENTS

| | | |
|---|---|---|
| GB | 2 354 839 A | 4/2001 |
| GB | 2 370 653 A | 7/2002 |

OTHER PUBLICATIONS

English translation and the Office action of the German Patent Office dated May 25, 2012 in German patent application 10 2011 114 752.0 on which the claim of priority is based.

International Search Report dated Jan. 7, 2013 of international application PCT/EP2012/004026 on which this application is based.

\* cited by examiner $z_{SF}(r, phi)$ phase_spiral(r,phi)

phase_spiral(r,phi)

LENS HAVING AN EXTENDED RANGE OF FOCUS AND METHOD OF MAKING THE SAME

CROSS REFERENCE TO RELATED APPLICATIONS

This application is a continuation application of international patent application PCT/EP2012/004026, filed Sep. 26, 2012, designating the United States and claiming priority from German application 10 2011 114 752.0, filed Sep. 29, 2011, and the entire content of both applications is incorporated herein by reference.

FIELD OF THE INVENTION

The invention relates to a lens which has an extended range of focus, wherein the lens consists of a solid material, the optical surfaces of the lens are transparent and the lens has a focal power distribution. The invention furthermore relates to a method for producing the lens and to the use thereof for influencing the imaging of an image onto the retina of an eye and to the use thereof in a lens system with an extended range of focus.

BACKGROUND OF THE INVENTION

Multifocal lenses should simultaneously meet a number of demands. Initially, a sufficiently good contrast transfer function in two or more focal planes should be ensured. Furthermore, the contrast transfer function should be independent of the size of the pupil. And finally, it should be easy to make the lens; it should not have projections or edges, and therefore have curves which are as smooth as possible.

Such lenses are used, in particular, for correcting visual defects by means of spectacle lenses or as intraocular lenses (IOLs).

In contrast to the monofocal IOLs, which were already introduced many years ago, multifocal lenses were previously only implemented for the bifocal case since there are significant problems in satisfying the aforementioned demands simultaneously. Here, a variant is based upon a special rotationally symmetric ring system, wherein there is sufficiently good imaging for two discrete object-side focal planes, for example at 0 dpt and at a corrective power of approximately 3 dpt, by skillful matching of ring radii, ring widths and ring depths.

Such a bifocal lens is described in U.S. Pat. No. 5,982,543 A and uses a rotationally symmetric Fresnel-like ring system.

U.S. Pat. No. 6,120,148 A describes a rotationally symmetric diffractive ring system. The bifocal lens from U.S. Pat. No. 6,536,899 B1 likewise utilizes a ring system, wherein each ring consists of two sub-rings, which respectively realize the two desired focal lengths.

In a slightly modified form, solutions are also derived herefrom, in which a single lens covers an extended, continuous range of focus. Such lenses are also known by the term "extended depth of focus lens" or else as "EDoF lens". In United States patent application publication 2006/0176572 A, use is made of a rotationally symmetric system of rings, wherein the individual focal lengths of the rings lie within the desired continuous focal length range. The "extended depth of focus" effect is created by mixing the various focal lengths.

The system in accordance with United States patent application publication 2011/0279912 consists of sectors ("pie slices") with a focal power increasing in the azimuth direction. Here, the focal power distribution has discrete steps between the sectors.

United States patent application publication 2010/0002310 A1 describes an optical imaging system for a camera which has an extended depth of field range. The extended depth of field is achieved by a combination of several lenses with aspherical surfaces.

A disadvantage in the case of intraocular lenses in particular is that a strong radius curvature is required when using "normal" spherical or aspherical basic lens shapes due to the relatively short focal length caused by the length of the eye. This creates a large lens thickness, a relatively large lens volume with a correspondingly large weight. Since intraocular lenses are manufactured from organic polymers, the refractive index is usually relatively low, leading to a strong radius curvature and hence also a relatively thick lens shape.

SUMMARY OF THE INVENTION

It is an object of the invention to provide a novel lens with an extended range of focus. The novel lens should provide, either individually, in particular as an intraocular lens, or in conjunction with other optical components, optical systems which, while having a sufficiently good imaging quality, provide a large depth of field range. It should be possible to produce the novel lens in a cost-effective manner.

In particular, the novel lens is to have a reduced lens thickness at a given focal power when used as an intraocular lens.

The lens with an extended range of focus includes a solid, transparent material and has two manufactured optical surfaces. According to the invention, the lens has a focal power distribution $F_{tot}$ which, in relation to a plane perpendicular to the optical axis, is a function of the radial height r and of the azimuth angle of the aperture phi and changes between a basic value of the focal power $F_{lens}$ not equal to zero and a maximum value $F_{spiral\ max}$. Hence, the focal power distribution emerges as $$F_{tot}(r,phi) = F_{lens} + F_{spiral}(r,phi),$$

with the spiral focal power component $$F_{spiral}(r,phi) = F_{spiral\ max}(r,phi) * w(phi),$$

where $F_{spiral\ max}(r, phi)$ depends nonlinearly on the radius and $w(phi)$ is a factor for the focal power component with a spiral profile.

An essential further aspect of the invention is that a value of the focal power of the lens $F_{lens}$ is split into a focal power component of a refractive base system of the lens $F_{base}$ and a structure-shaped focal power component $F_{structure}$, such that $$F_{lens}(r) = F_{base}(r) + F_{structure}(r)$$

applies. Here, $F_{base}$ is a base focal power of a lens, which is determined by lens radii or free-form surface polynomials and lens thickness, as well as refractive index of the lens material, and $F_{structure}$ is a focal power which is not described by lens radii or free-form surface polynomials and lens thickness, as well as refractive index of the lens material. Therefore, the term "structure" and the symbol $F_{structure}$ is defined in this document as focal power of a structure which is present as a height profile $z_{Fresnel}$ of a Fresnel lens in a first case, is present as a phase profile phase$_{structure}$ of a diffractive optical element (DOE) in a second case or is present as refractive index gradient $\Delta n_{structure}$ of a gradient index lens (GRIN lens) in a third case. Therefore, the focal power distribution of the lens according to the invention emerges in the rotationally symmetric case as $$F_{tot}(r,phi) = F_{base}(r) + F_{structure}(r) + F_{spiral\ max}(r,phi) * w(phi). \quad 5$$

However, both the base focal power of the lens $F_{base}$ and the focal power of the structure $F_{structure}$ may have the focal power profile of a free-form surface, wherein the corresponding polynomials are then to be inserted into the equations.

The invention therefore relates to a special, novel lens shape, by means of which it is possible simultaneously to cover a predetermined focal length range, that is, to generate a sufficiently good image quality over an extended range of focus. What dividing the basic value of the focal power of the lens $F_{lens}$ into the base focal power $F_{base}$ of the lens to be manufactured and into the focal power of a structure $F_{structure}$ realizes is that the lens to be manufactured can be produced with flatter radii. As a result of this, there is a significant reduction in the lens thickness, hence of the lens volume, and therefore also of the lens weight. Such lenses with an extended range of focus find use in optical systems for a camera, a microscope or in optical measurement apparatuses.

A main field of application is an intraocular lens with a variable focal length range. Using the spiral focal power component, it is possible to realize a focusing range from 0 to approximately 3.5 dpt in relation to a fixed base focal power. Such an intraocular lens is usually implanted into the eye after removing the natural lens. However, it can also be employed in addition to the natural lens.

The lens of the invention is made according to the following steps:

Step 1: calculating an initially monofocal, virtual base system, which adopts the focusing for a fixed diopter setting (for example, 60 dpt for the healthy human eye in the case of an IOL). This is the basic value of the focal power $F_{lens}$, which is set by the surface forms of the optical surfaces, the lens thickness and a material type.

Step 2: dividing the basic value of the focal power $F_{lens}$ into a base focal power $F_{base}$ and into the focal power of a structure $F_{structure}$.

In practice, it was found to be expedient to realize more than 50% of the basic value of the focal power $F_{lens}$ as refractive base focal power $F_{base}$ and to realize less than 50% of the basic value of the focal power $F_{lens}$ as focal power of the structure $F_{structure}$. In respect of the occurrence of defects, it is particularly advantageous to realize more than 70% as refractive base focal power $F_{base}$ and less than 30% as focal power of the structure $F_{structure}$. The lens to be manufactured with the base focal power $F_{base}$ corresponds to a conventional lens with two optical surfaces, which can be embodied spherically and/or aspherically and/or as a free-form surface. At least one of these optical surfaces serves as base surface for realizing the additional focal power distribution, which will be described in the next step but one, step 4.

Step 3: determining the parameters of the additional spiral and structure-shaped focal power $F_{SS}$ by adding the spiral focal power distribution $F_{spiral}$ to the focal power of the structure $F_{structure}$.

Step 4: adding or subtracting the spiral and structure-shaped focal power distribution $F_{ss}(r, phi) = F_{structure}(r) + F_{spiral}(r, phi)$ obtained in step 3 to the optical effect of the base system $F_{base}$. As a result, the focal power of the lens changes nonlinearly, depending on the radius, with the azimuth angle of the aperture.

"Adding" the spiral and structure-shaped focal power distribution can be brought about by several variants, which can each be used individually or together in any combination:

a) "Adding" a spiral and Fresnel-shaped height profile $z_{SF}(r, phi)$, which has the spiral and structure-shaped focal power distribution $F_{SS}$, to one of the optical surfaces of the lens with the base focal power $F_{base}$ calculated in step 2. This determined optical surface is the only calculated base surface with the height profile $z_{base}$, to which the spiral and Fresnel-shaped height profile $z_{SF}(r, phi)$ is added and thus the profile to be manufactured of this optical surface is set.

b) "Adding" a spiral and structure-shaped diffractive structure with the additional focal power $F_{SSdiffractive}$ to one of the calculated and manufactured optical surfaces of the lens with the base focal power $F_{base}$ in accordance with step 2.

c) "Adding" a spiral and structure-shaped refractive index profile $\Delta n_{SS}$ in the material of the lens. In this case, the calculated surfaces in accordance with step 2 are not modified and manufactured thus.

Step 5: Producing the first optical surface and the second optical surface of the lens with the base focal power $F_{base}$, including the application or the introduction of the spiral and structure-shaped focal power distribution at and/or on and/or inside the lens.

Production methods for the spiral and structure-shaped focal power distribution are in particular:

aa) producing the optical surface by hot stamping or injection molding
ab) producing the optical surface by diamond turning
ba) production by lithographic etching methods on the optical surface
bb) production by diamond turning on the optical surface
ca) production by centrifugal casting from the liquid state
cb) production by ion implantation.

The variants a) and/or b) can be applied to one optical surface or else to both optical surfaces of a lens in a manner splitting the effect. Diffractive optical elements can be used additionally or together with the generation of the focal power distribution for color correction. The scope of the invention also includes other methods and measures, by means of which the spiral and structure-shaped focal power distribution according to the invention can be obtained in a lens, for example by the introduction of nanoparticles.

As a result of the above-described procedure, a continuous variation of the additional spiral focal power $F_{spiral}$ to the focal power of the base system of between 0 and approximately 3.5 dpt is achieved in e.g. an intraocular lens with, in many cases of application, a sufficiently good image quality. As a result of the focal power component of the structure $F_{structure}$, a reduction in the lens thickness by up to 50% is achieved, leading to a reduction in volume and weight of approximately the same order of magnitude.

The radius-dependent and azimuth angle-dependent focal power $F_{tot}(r, phi)$ emerges from the sum of a basic focal power of the base system $F_{base}$, from the focal power of the additional structure $F_{structure}$ and from the additional spiral focal power $F_{spiral}(r, phi)$ which is dependent on the radius and the angle. Thus, in the rotationally symmetric case, the following applies:

$$F_{tot}(r, phi) =$$

$$F_{base}(r) + [F_{structure}(r) + F_{spiral}(r, phi)] = \frac{1}{f_{base}} + \left[\frac{1}{f_{structure}} + \frac{1}{f_{spiral}}\right].$$

Since standardized optical methods are used for producing the lens with the extended range of focus, this lens can be produced in a cost-effective manner.

In the case a) of "adding" a spiral and Fresnel-shaped height profile to one of the optical surfaces of the lens and thereby realizing a spiral and Fresnel-shaped focal power distribution of the overall system, the following observations apply:

The overall focal power $F_{tot}$ is composed by adding together the basic focal power of the base system $F_{base}$, the focal power of the Fresnel lens $F_{Fresnel\ Fresnel}$ and the additional spiral focal power $F_{spiral}$.

$$F_{tot}(r,phi) = F_{base} + F_{Fresnel} + F_{spiral}(r,phi),$$

where, for manufacturing reasons, there is a combination into the base focal power component of the lens $F_{base}$ and into the spiral and Fresnel-shaped focal power component $$F_{SF}(r,phi) = F_{Fresnel} + F_{spiral}(r,phi).$$

Since the distribution of the additional focal power is obtained by a height distribution in this case, the following applies:

$$z_{tot}(r,phi) = z_{base} + z_{SF}(r,phi).$$

The height profile, which supplies the spiral and Fresnel-shaped additional focal power, is, in general, described by $$z_{SF}(r,phi) = z_{Fresnel} + z_{spiral}(r,phi)$$

The basic focal power of the base system emerges for spherical lenses from the equation $$F_{base} = \left[\frac{n2-n1}{n1} * \left(\frac{1}{R3} - \frac{1}{R4}\right) + \frac{(n2-n1)^2 * d}{n1*n2*R3*R4}\right].$$

Here, $R_3$ is for example the radius of the first optical surface which is produced in reality and $R_4$ is the radius of the calculated base surface, to which the additional spiral and Fresnel-shape focal power $F_{SF}$ in the form of the height profile $z_{FS}$ is "added" (the additive height $z_{SF}$, which supplies the additional focal power, can also be added to the radius $R_3$ or can be split over both radii $R_3$ and $R_4$; the equations then have to be modified accordingly).

The height profile $z_{base}$ for the calculated base surface with the radius $R_4$ of the spherical lens emerges as $$z_{base}(x,y) = R_4 - \sqrt{R_4^2 - x^2 - y^2}, \text{ and, with } r = \sqrt{x^2 + y^2},$$

the data of the base surface in polar coordinates emerge as $$z_{base}(r) = R_4 - \sqrt{R_4^2 - r^2}.$$

Thus, for the case of a spherical base surface and a rotationally symmetric Fresnel structure, the following applies:

$$z_{tot}(r,phi) = (R_4 - \sqrt{R_4^2 - r^2}) + [z_{Fresnel}(r) + z_{spiral}(r,phi)].$$

The rotationally symmetric, Fresnel-shaped additional focal power is calculated as $$z_{Fresnel}(r) = \sum_{l=2}^{L} e_1 * r^l \text{ or } z_{Fresnel}(r) = \sum_{l=1}^{L} e_1 * r^{2*l}.$$

To the extent that non-spherical base surfaces underlie the lens, the known polynomials for describing non-spherical surfaces are used for determining the optical surfaces and/or the base surface.

By the additive term $z_{SF}(r, phi)$, the spiral and Fresnel-shaped additional focal power is produced as material height, which is added to or else subtracted from the optical base surface with the radius $R_4$. Analogous considerations also apply to aspherical and free-form surfaces, which cannot be described by a simple radius specification.

The spiral height profile emerges from $$z_{spiral}(r,phi) = z_{spiral\ max}(r) * w(Phi),$$

where
the radial polynomial for the maximum spiral height component as a function of the radius $z_{spiral\ max}(r)$, which embodies the maximum diopter number to be obtained, is:

$$z_{spiralmax}(r) = \sum_{j=2}^{N} c_j * r^j,$$

where r is the radial height and $c_j$ is a coefficient set of the radial polynomial.

In the simplest case, $$w(phi) = \frac{phi}{2\pi}$$

is the angle-dependent, linear normalized component, with phi as azimuth angle on the base surface of the base system (carrier lens).

The additive term $z_{spiral}(r, phi)$, which is added to the base surface of the lens, emerges from $$z_{spiral}(r, phi) = z_{spiralmax}(r) * w(phi) = \sum_{j=2}^{N} c_j * r^j * \frac{phi}{2\pi}.$$

In general, the height component of the focal power of the overall system of the lens is obtained as $$z_{tot}(r, phi) = z_{base}(r) + [z_{Fresnel}(r) + z_{spiral}(r, phi)]$$

$$z_{tot}(r, phi) = z_{base} + \left[\sum_{l=2}^{L} e_1 * r^l + \sum_{j=2}^{N} c_j * r^j * \frac{phi}{2\pi}\right].$$

For the radial polynomial $z_{spiral\ max}(r)$, the approach $$z_{spiralmax}(r) = \sum_{j=1}^{N} c_j * r^{2*j}$$

can also be used in an analogous manner and likewise $$z_{Fresnel}(r) = \sum_{l=1}^{L} e_l * r^{2*l}$$

is possible.

In the simplest case, it is therefore already sufficient to realize the additional radial focal power distribution as a product of the normalized azimuth angle and the maximum diopter number to be achieved.

For the simplest case of the radial polynomial $$z_{spiral\,max}(r) = c_1 * r^2,$$

with c1 as coefficient in front of the quadratic term, the equation for the additive term thus reads $$z_{spiral}(r, phi) = z_{spiral\,max}(r) * w(phi) = c_1 * r^2 * \frac{phi}{2\pi}.$$

The procedure described above represents a linear "helical increase". In this form, the imaging quality is good with approximately no change over the whole diopter region.

However, it is often desirable to prefer specific diopter regions such as e.g. the zero diopter position. To this end, it is necessary to depart from the linear dependence of the z-height on the angle.

In general, the angle-dependent component can be described by the equation $$w(phi) = \sum_{i=1}^{M} I_i * \exp[-a_i * (phi - w_i)^2],$$

where $w_i$ are the peak positions (between 0 and $2\pi$), $I_i$ are the peak intensities and $a_i > 0$ are the damping coefficients for the respective peak positions.

By way of example, for M=1; $I_1$=1 and $w_i$=$2\pi$, the function $$z_{spiral}(r, phi) = z_{spiral\,max}(r) * w(phi) = \sum_{j=2}^{N} c_j * r^j * \exp[-a_1 * (phi - 2\pi)^2]$$

with $a_1$=0.25 allows a preference for the zero diopter region to be implemented. The small increase between phi=0 and phi=2 causes a small addition of focal power in this angular range and hence a larger surface component for the zero diopter distance.

In the context of optimizing the lens with the extended range of focus, further advantages can be obtained by virtue of further degrees of freedom being available during the design. By way of example, this is brought about if the radial function $z_{spiral\,max}(r)$ likewise obtains an azimuth-dependent set of coefficients and hence the radial polynomial $z_{spiral\,max}(r, phi)$ is determined as $$z_{spiral\,max}(r, phi) = \sum_{j=2}^{N} c_j(phi) * r^j.$$

From this, the additive term $z_{spiral}(r, phi)$ emerges in general as $$z_{spiral}(r, phi) = z_{spiral\,max}(r, phi) * w(phi) = \sum_{j=2}^{N} c_j(phi) * r^j * \sum_{i=1}^{M} I_i * \exp[-a_i * (phi - w_i)^2].$$

Hence, it is possible to specify further variants from the general equation $$w(phi) = \sum_{i=1}^{M} I_i * \exp[-a_i * (phi - w_i)^2]$$

for the angle term w(phi), by means of which it is possible to control the "effective period" of the individual azimuth ranges.

The explanations above were all based upon an additive term which is refractive and which is added to one of the optical surfaces of the base system.

The addition term can naturally also be available in a diffractive form, that is, a diffractive optical element (DOE) with a spiral and structure-shaped phase function is applied to the spherical carrier surface of the base system (case b)). This phase function is designed in a completely analogous fashion to the refractive approach. Blaze gratings, sinusoidal gratings and binary gratings are particularly suitable.

In a radial and angle-dependent manner, the grating frequency changes spirally continuously from an initial value to a maximum value corresponding to the maximum focal power.

The spiral phase function emerges as $$phase_{spiral}(r, phi) = phase_{max}(r) * w(phi) = \sum_{j=2}^{N} k_j * r^j * w(phi)$$

or $$phase_{spiral}(r, phi) = phase_{max}(r) * w(phi) = \sum_{j=1}^{N} k_j * r^{2*j} * w(phi).$$

The spiral focal power of the diffractive structure emerges as $$F_{spiral\,diffractive} = 2k_2 \frac{\lambda}{wl} * w(phi)$$

or as $$F_{spiral\,diffractive} = 2k_1 \frac{\lambda}{wl} * w(phi),$$

where wl is the design wavelength of the diffractive optical element and $\lambda$ is the application wavelength. The term w(phi) can be selected from the explanations above and is $$\frac{phi}{2\pi}$$

in the simplest case. With $k_1$ as coefficient of the quadratic term, the maximum focal power emerges as $$F_{spiral\ max\ diffractive} = 2k_1 \frac{\lambda}{w1}$$

and the angle-dependent term $F_{spiral\ diffractive}$(phi) emerges as $$F_{spiral\ diffractive} = 2k_1 \frac{\lambda}{w1} * \frac{phi}{2\pi}.$$

In the diffractive embodiment, the structure producing the additional focal power is a phase function. The phase of a rotationally symmetric structure is $$phase_{structure}(r) = \sum_{l=2}^{L} g_1 * r^l$$

or $$phase_{structure}(r) = \sum_{l=1}^{L} g_1 * r^{2*l}.$$

In the diffractive embodiment, the focal power of the rotationally symmetric structure is $$F_{structure\ diffractive} = 2g_2 \frac{\lambda}{w1}$$

or is $$F_{structure\ diffractive} = 2g_1 \frac{\lambda}{w1},$$

where w1 is the design wavelength of the diffractive optical element and $\lambda$ is the application wavelength.

In the simplest case, the overall focal power of the lens emerges for N=1 and L=1 from a comparatively strong refractive basic focal power $F_{base}$ of the monofocal base system and a relatively small focal power component of the diffractively produced spiral and rotationally symmetric additional focal power $F_{SS\ diffractive}$:

$$F_{tot} = F_{base} + [F_{structure\ diffractive} + F_{spiral\ diffractive}] = F_{base} + F_{SS\ diffractive}$$

$$F_{tot} = F_{base} + \left[2g_1 \frac{\lambda}{w1} + 2k_1 \frac{\lambda}{w1} * w(phi)\right].$$

In practical terms, the base focal power of the lens $F_{base}$ is produced first and the spiral and structure-shaped additional focal power $F_{SS\ diffractive}$ is applied onto an optical surface of the base lens.

Thus, as a result of the diffractive component, a relatively only small color aberration is created and the lens with the extended range of focus is also suitable for white light.

The spiral and structure-shaped additional focal power $F_{SS\ diffractive}$ can also be divided onto both optical surfaces of the lens.

However, the spiral and structure-shaped addition term $F_{ss}$ can also be realized by producing a spiral and structure-shaped refractive index gradient $\Delta n_{SS}$ (case c)). By way of example, DE 10 2009 033 984 A1 describes how inhomogeneous optical properties can be generated in an optical material. In a development of the method described therein, it is also possible to realize a spiral and structure-shaped refractive index profile. The properties and the design of the refractive index gradient in this case are brought about in a completely analogous fashion to the refractive approach and to the diffractive approach.

The overall focal power $F_{tot}$ emerges from the base focal power $F_{base}$ of the monofocal base system plus the additional focal power $F_{SS}$ which is provided by the spiral and structure-shaped focal power increase.

The spiral and structure-shaped additional focal power $F_{SS}$(r, phi) is proportional to the refractive index difference $\Delta n_{SS}$(r, phi) according to the equation $$\Delta n_{SS}(r, phi) =$$
$$\Delta n_{structure} + \Delta n_{spiral}(r, phi) = \Delta n_{structure} + \Delta n_{spiral\ max}(r, phi) * w(phi).$$

The refractive index difference $\Delta n_{SS}$(r, phi) increases continuously from 0 (at r=0 and phi=0) to the maximum refractive index increase $\Delta n_{spiral\ max}$(at r=D/2 and phi=2$2\pi$), wherein the function w(phi) can predetermine the above-described linear or general profile.

Here, $\Delta n_{spiral\ max}$(r, phi) is calculated analogously to the height $z_{spiral\ max}$ or to the phase function $phase_{spiral\ max}$ and can be both positive and negative in relation to the base refractive index $n_2$ of the lens.

The subject matter of the present invention therefore also relates to any mixed forms of spiral and/or Fresnel-shaped height profile(s), of spiral and/or rotationally symmetric phase profile(s) and/or of spiral and/or rotationally symmetric refractive index profile(s), which produce the desired additional focal power profile.

The height profile and/or the phase profile can be distributed on one of the optical surfaces and/or on both optical surfaces of a lens, or can be arranged in combination.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
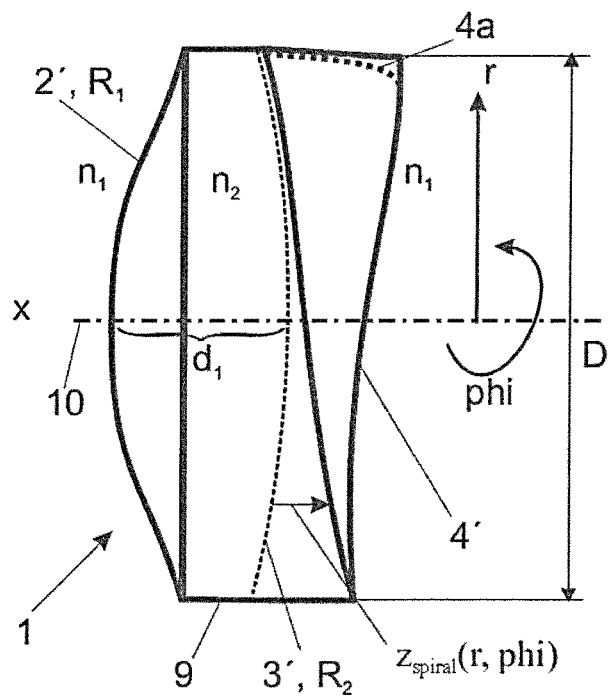
FIG. 1 is a side view of a "thick" lens having an extended range of focus according to a solution described in DE 10 2011 101 899 A1.

FIG. 1 shows a "thick" lens 1 having an extended range of focus as disclosed in DE 10 2011 101 899 A1, the content of which is incorporated by reference. Shown is a side view with a depiction of the spiral refractive height profile $z_{spiral}$ (r, phi), which produces the spiral focal power distribution $F_{spiral}$(r, phi). This lens 1 is initially determined by its base system with the radius $R_1$ of the first optical surface 2' and the radius $R_2$ for the calculated base surface 3', and also by the lens thickness $d_1$ and the refractive index $n_2$. These parameters are determined for an envisaged basic magnification. An additional material thickness z is "added" to the calculated shape of the base surface 3' with the radius $R_2$, with the additional material thickness being z=0 mm at phi=0, then increasing continuously and having a maximum value in the millimeter range at phi=2π. In practice, the maximum value will lie slightly in front of the azimuth angle phi=2π in order to realize a continuous, albeit very steep, transition back to the value zero at phi=0, as indicated by the dashed curve denoted by 4a.

Parameters for a lens are specified as an example:

$R_1$=−15.1411 mm radius to be produced
$R_2$=22.3164 mm calculated radius
$d_1$=0.8 mm
$n_1$=1 (refractive index outside of the lens)
$n_2$=1.56 (refractive index of the lens medium) hence, from the equation $$f_{base} = \frac{1}{\left[\frac{n2-n1}{n1}*\left(\frac{1}{R1}-\frac{1}{R2}\right)+\frac{(n2-n1)^2*d1}{n1*n2*R1*R2}\right]}$$

wherein the focal length of the "base lens" emerges as 16.233 mm.

A linear "helical increase" in accordance with the equation $$z_{spiral}(r, phi) = z_{spiral\,max}(r)*w(phi) = c_1 * r^2 * \frac{phi}{2\pi}$$

as a continuous, spiral height profile with a linear profile is added to the calculated base surface with the radius $R_2$=22.3164 mm and results in the optical surface 4'.

With $c_1$=−0.013, a spiral addition which increases the focal length in air up to 20.57 mm, corresponding to 3.5 dpt, is obtained.

Figure 2:
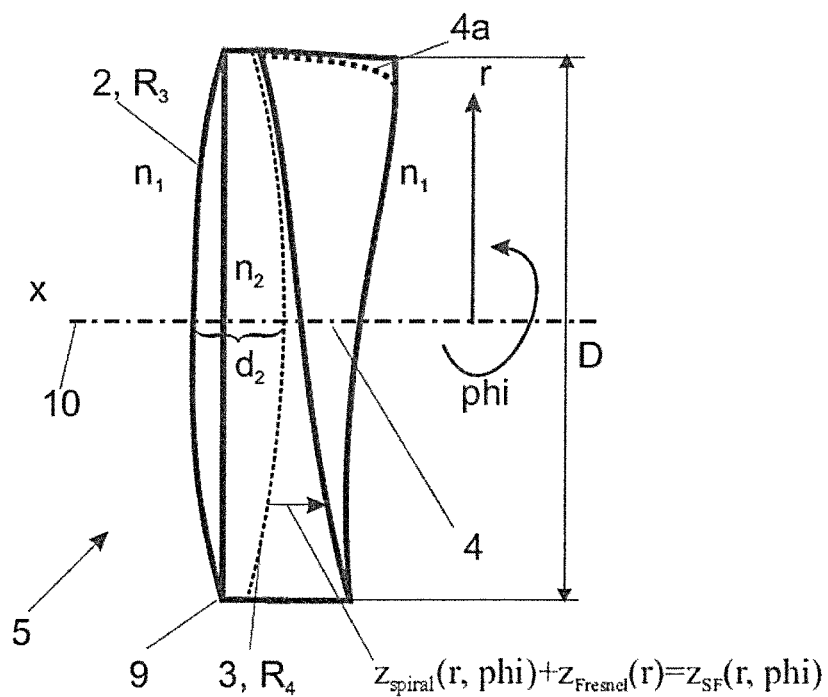
FIG. 2 is a side view of a "thin" lens having an extended range of focus in accordance with the invention.

FIG. 2 shows a "thin" lens 5 according to the invention, which, compared to the lens 1 shown in FIG. 1, has flatter radii $R_3$ and $R_4$ and the central thickness $d_2$ of which is thinner, wherein approximately the same imaging parameters are obtained as in the case of the lens as per FIG. 1: in the case of a basic focal power of approximately 61 dpt, an additional focal power of 3.5 dpt is achieved. The "thin" lens 5 has the peculiarity that the spiral addition contains a rotationally symmetric Fresnel component. This Fresnel component realizes part of the focal power which the "thick" lens 1 as per FIG. 1 obtains from the radii $R_1$ and $R_2$ and also from the lens thickness $d_1$, and so the radii $R_3$ and $R_4$ of the novel lens 5 are flatter and the central thickness $d_2$ thereof is comparatively smaller.

The procedure for designing the novel "thin" lens 5 according to the invention will be explained on the basis of FIG. 3.

Figure 3:
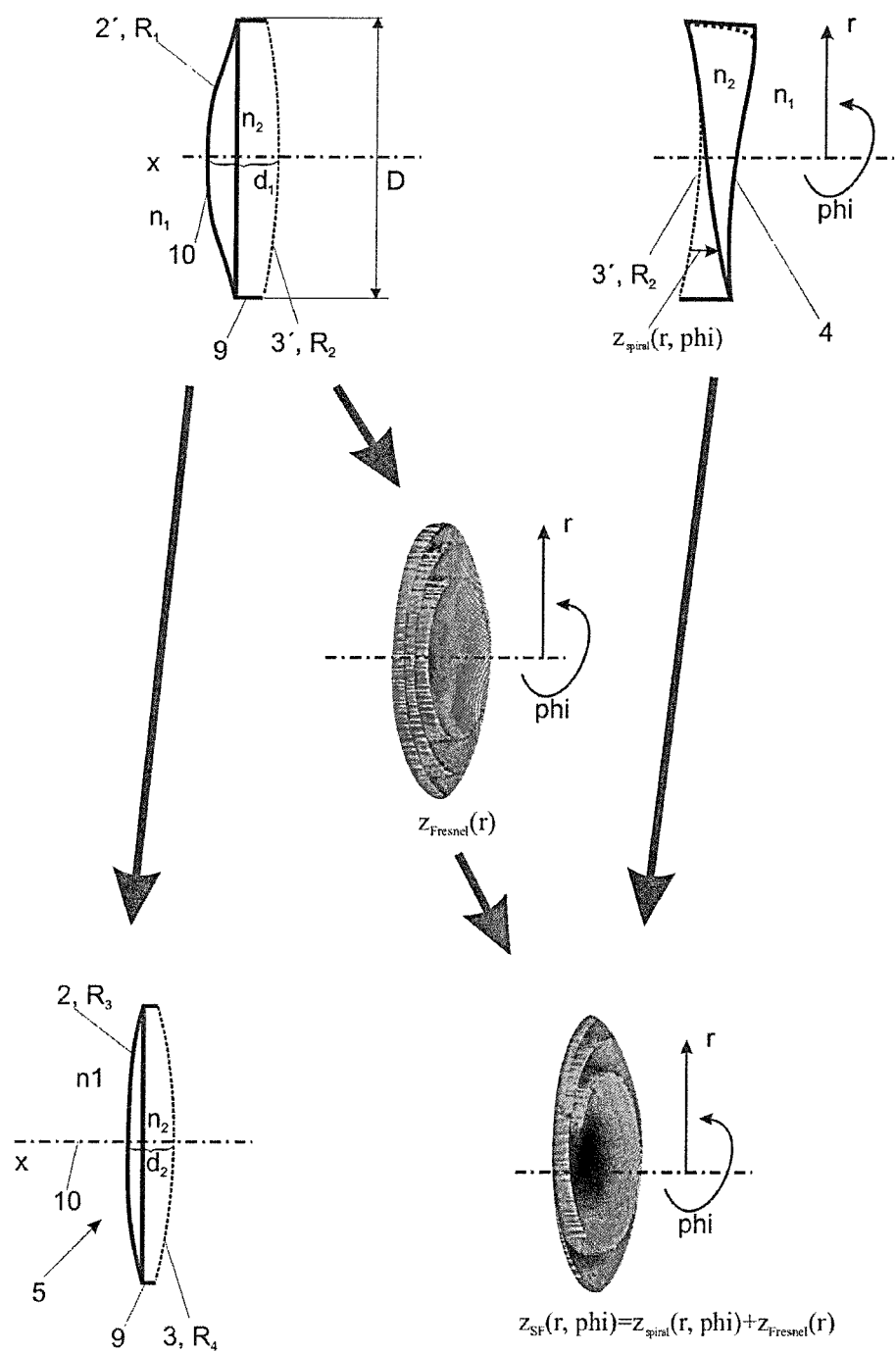
FIG. 3 is a schematic of the procedure and the calculation steps leading to design and production of the "thin" lens.

The start point is the "thick" lens 1 depicted in the upper row of FIG. 3, which is only calculated. It consists of the refractive base system with the radii $R_1$ and $R_2$ and also the central thickness $d_1$ (depicted on the left) and the spiral focal power component, which is theoretically realized by the height profile $z_{spiral}$(r, phi) on the radius $R_2$ (depicted on the right). What is then depicted below is that the focal power of the refractive base system is split into a novel "thin" lens 5, with the radii $R_3$ and $R_4$ and also with the central thickness $d_2$, and into a rotationally symmetric Fresnel-shaped focal power component $z_{Fresnel}$(r).

The lowest row depicts that the Fresnel-shaped focal power component $z_{Fresnel}$(r) and the spiral component $z_{spiral}$ (r, phi) are added to form a spiral and Fresnel-shaped additional focal power $F_{SF}$. The height profile $$z_{SF}(r,phi)=z_{spiral}(r,phi)+z_{Fresnel}(r)$$

is added to the only calculated radius $R_4$ of the base lens with the height profile $z_{base}$. Now, a lens is produced with the radius $R_3$, with a central thickness $d_2$ and with a height profile $z_{SF}$(r, phi) on the calculated radius $R_4$. The corresponding height profile of the optical surface 4 to be manufactured emerges as $$z_{tot}(r,Phi)=(R_4-\sqrt{R_4^2-r^2})+[z_{Fresenel}(r)+z_{spiral\;max}(r,phi)*w(phi)].$$

Figure 4:
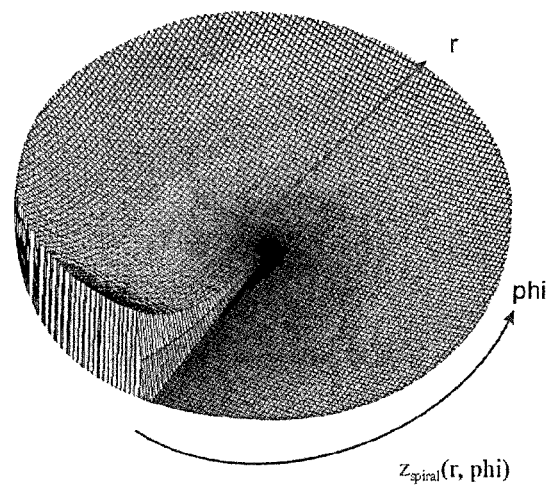
FIG. 4 depicts a spiral focal power component.
Figure 5:
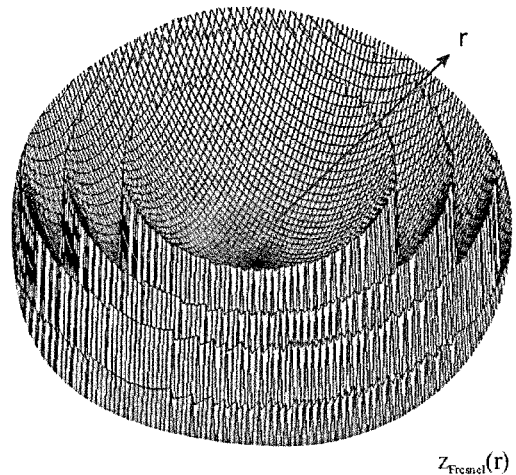
FIG. 5 depicts a rotationally symmetric focal power component, made to be a Fresnel-type.
Figure 6:
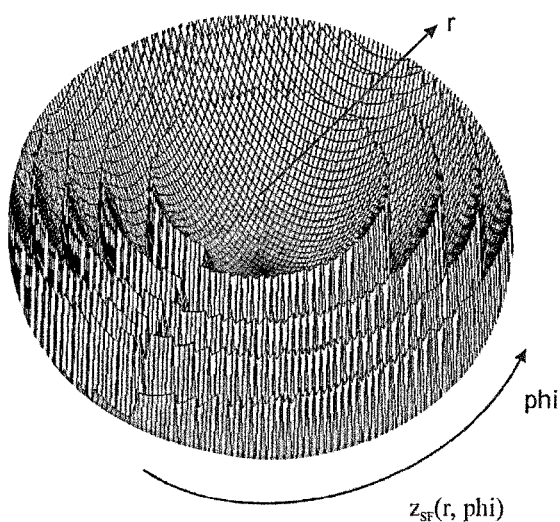
FIG. 6 depicts the added spiral and rotationally symmetric focal power component, made to be a Fresnel-type.
Figure 7:
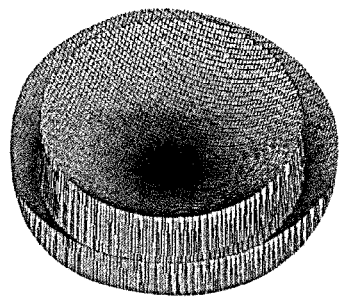
FIGS. 7 to 10 are depictions of the added spiral and rotationally symmetric focal power component, made to be a Fresnel-type, wherein the power of the spiral component increases from figure to figure.
Figure 8:
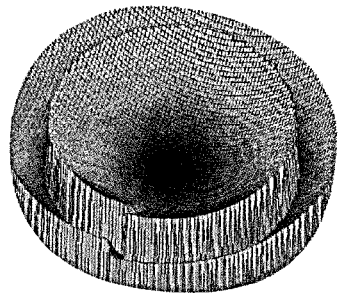
Figure 9:
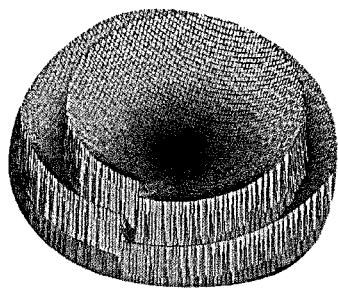
Figure 10:
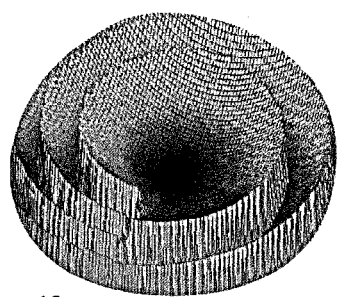

FIG. 4 shows only the spiral focal power component $F_{spiral}$ of the lens as height profile $z_{spiral}$(r, phi). FIG. 5 shows only the rotationally symmetric focal power component $F_{Fresnel}$, made to be Fresnel-type, of the lens as height profile $z_{Fresnel}$(r). The depiction in FIG. 6 shows the result of adding the spiral focal power component and the rotationally symmetric focal power component, made to be Fresnel-type, as height profile $z_{SF}$(r, phi), which represents the spiral and Fresnel-shaped focal power component $F_{SF}$.

This height profile is added to the height profile $z_{base}$ of the calculated base surface 3 with the radius $R_4$ and manufactured on the lens to be produced.

FIGS. 7 to 10 each show a depiction of the added spiral and rotationally symmetric focal power component $F_{SF}$, made to be Fresnel-type, wherein the power of the spiral component increases from 1 dpt to 3.5 dpt from figure to figure.

Figure 11:
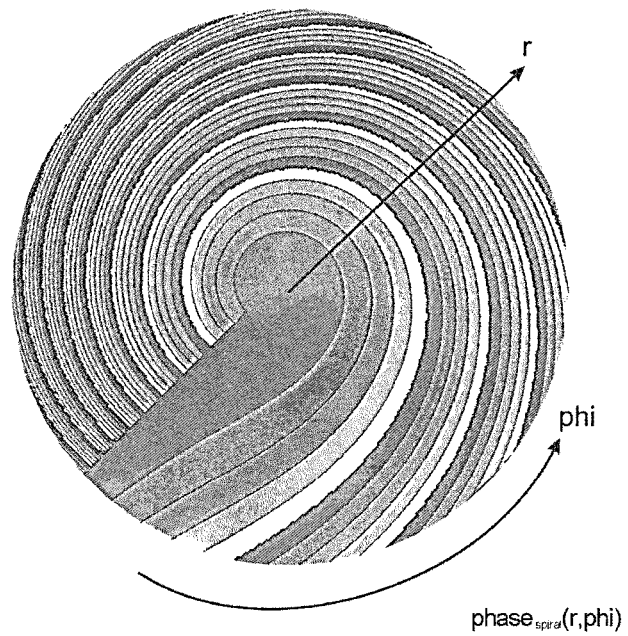
FIG. 11 depicts a diffractive, spiral structure which produces the spiral focal power component.
Figure 12:
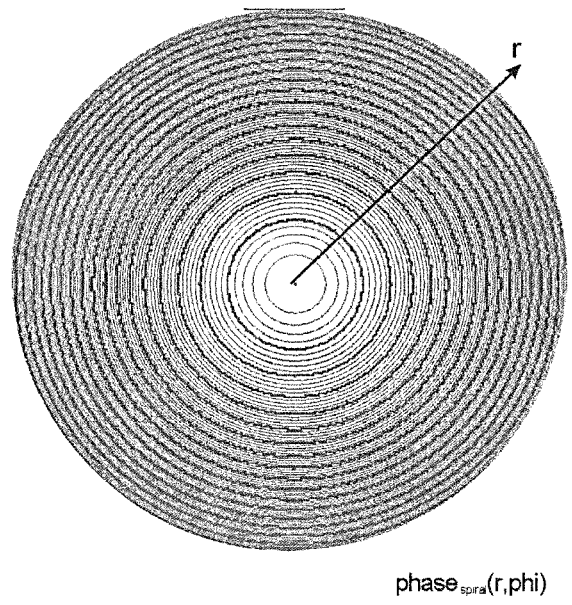
FIG. 12 depicts a diffractive, rotationally symmetric ring structure.
Figure 13:
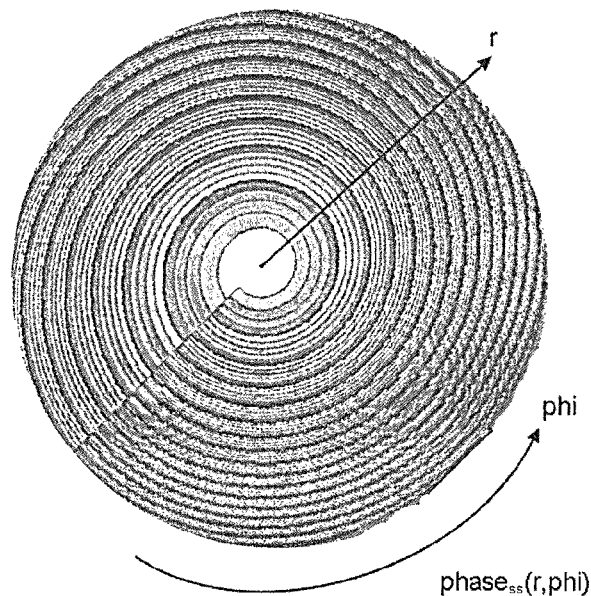
FIG. 13 depicts the added diffractive, spiral structure and the diffractive, rotationally symmetric ring structure, which corresponds to the focal power component as per FIG. 6.

Subsequently, FIGS. 11 to 13 show that a spiral and structure-shaped additional focal power of the lens $F_{SS}$ is transferred in a completely analogous manner onto a diffractive approach starting from the refractive approach (where the structure-shaped additional focal power is realized by a Fresnel structure).

FIG. 11 schematically shows a diffractive, spiral structure which produces the spiral focal power component $F_{spiral\;diffractive}$. FIG. 12 schematically shows a diffractive, rotationally symmetric ring structure which produces the structure-shaped focal power component $F_{structure\;diffractive}$. FIG. 13 shows the result of adding the two diffractive structures. This superposition of the diffractive, spiral structure and the diffractive, rotationally symmetric ring structure provides as a result a spiral and structure-shaped focal power component $F_{SS}$, which, in terms of its effect, corresponds to the refractive spiral and Fresnel-shaped focal power component $F_{SF}$, which is schematically depicted by the spiral and Fresnel-shaped height profile $z_{SF}$ in FIG. 6.

Figure 14:
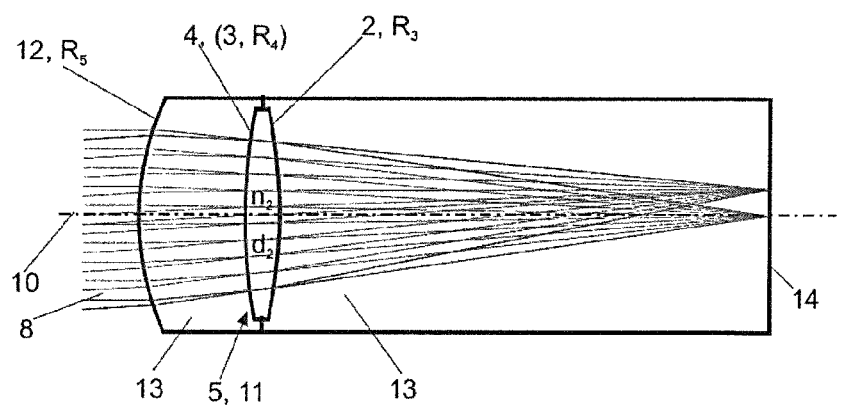
FIG. 14 shows a schematic depiction of an intraocular lens in the eye.

FIG. 14 shows a schematic depiction of an intraocular lens 11, which is implanted in the eye as "thin" lens 5 with extended range of focus. In the example, this lens replaces the natural lens of the eye and is situated in the light path between the cornea 12 and the retina 14 in the aqueous humor 13.

The intraocular lens 11 has a spherical first optical surface 2 and the second optical surface 4 carrying the spiral and structure form.

In a first example, the intraocular lens 11 with the extended range of focus has the following parameters for the base system: the base radii of the carrier lens are the produced lens radius $R_3 = -20$ mm and the calculated lens radius $R_4 = +20$ mm of the base surface 3. The spiral and Fresnel-shaped height profile $z_{SF}(r, phi)$ will be is added onto the base surface 3 and manufactured accordingly as surface 4.

The focal power of the component, made to be Fresnel-type, of the basic focal power of the lens emerges from the height profile of a Fresnel structure $$z_{Fresnel}(r) = \sum_{l=1}^{L} e_l * r^{2*l}$$

and, for L=2, provides the coefficients of the rotationally symmetric Fresnel polynomial $e_1 = 0.036$ and $e_2 = -0.00018398$.

The focal power of the spiral additional focal power of the lens emerges from the height profile $$z_{spiral}(r, phi) = z_{spiral\,max}(r) * w(phi) = \sum_{j=1}^{N} c_j * r^{2*j} * \frac{phi}{2\pi}$$

and, for N=1, provides the coefficients of the spiral polynomial $c_1 = 0.025$.

Thus, the following emerges:

$$z_{SF}(r, phi) = z_{spiral}(r, phi) + z_{Fresnel}(r) = c_1 * r^2 * \frac{phi}{2\pi} + e_1 * r^2 + e_2 * r^4.$$

The indentation depth of the element p, made to be Fresnel-type, is selected with 0.1 mm and thus the spiral additional focal power, made to be Fresnel-type, emerges by means of the modulus function $mod(z_{SF}(r, phi), p)$.

Here, the corneal radius is assumed to be $R_5 = 7.814$ mm and the conic constant is assumed to be $K = -0.26$. The distance between the cornea 12 and the front side of the lens $R_4$ is 4.12 mm; the lens thickness of the intraocular lens is $d_2 = 0.65$ mm and the distance between the front side of the lens $R_2$ and the retina 14 is 18.1 mm. Benz25 with a refractive index of the lens medium $n_2 = 1.56$ is used as material.

The refractive index outside of the lens, of the aqueous humor 13, is $n_1 = 1.33$.

Compared therewith, the intraocular lens described in DE 10 2011 101 899, FIG. 4 in that case, has the following parameters:
$R_1 = -15.1411$ mm (produced first optical surface 2)
$R_2 = 22.3164$ mm (calculated base surface 3)
Lens thickness $d_1 = 0.8$ mm As a result, the novel lens according to the invention in accordance with the example in FIG. 14 is thinner by 0.15 mm, caused by the flatter radius $R_3$ compared to $R_1$.

In a second example in respect of FIG. 14, the intraocular lens 11 with the extended range of focus has the following parameters for a diffractive embodiment of the spiral and structure-shaped additional focal power $F_{ss}$ on an optical surface of the base lens:

Cornea: radius $R_5 = 7.814$ mm, aspherical conic constant $K = -0.26$, base radii of the lens $R_3 = R_4 = +/-20.0$ mm (spherical); the distance between cornea $R_5$ and the manufactured optical surface 4 with the radius $R_4$ is 4.12 mm, the thickness of the intraocular lens $d_2 = 0.65$ mm and the distance between the manufactured optical surface 2 with the radius $R_3$ and the retina is 18.5 mm.

"Benz25" is used as material for the intraocular lens. The diameter of the intraocular lens is 6 mm. The refractive base system of the lens is described by these parameters and the focal power $F_{base}$ thereof is set. The spiral additional focal power $F_{spiral}$ and the structure-shaped additional focal power $F_{structure}$ are produced as a spiral and structure-shaped diffractive focal power distribution $F_{SS}$ using a diffractive optical element which is applied onto the surface with the radius $R_4$. Thus, the overall focal power of the intraocular lens 11 emerges as $$F_{tot} == F_{base} + F_{SS\,diffractive} =$$
$$F_{base} + [F_{structure\,diffractive} + F_{spiral\,diffractive}].$$

Expressed as a phase function, the spiral and structure-shaped additional focal power emerges as $$phase_{SS}(r, phi) = phase_{structure} + phase_{spiral},$$

with $$phase_{structure}(r) = \sum_{l=1}^{L} g_l * r^{2*l}$$

and $$Phase_{spiral}(r, phi) = Phase_{max}(r) * w(phi) = \sum_{j=1}^{N} k_j * r^{2*j} * w(phi).$$

With L=2, N=1 and $$w(phi) = \frac{phi}{2\pi},$$

the following emerges:

$$phase_{SS}(r, phi) = g_1 * r^2 + g_2 * r^4 + k_1 * r^2 \frac{phi}{2\pi}$$

and the reduced phase function emerges as $$\text{phase}_{SS\,reduced}(r,\,phi) = \frac{\text{phase}_{SS}(r,\,phi)}{wl} - \text{floor}\frac{\text{phase}_{SS}(r,\,phi)}{wl},$$

where phi=0 . . . 2π (azimuth angle), r=radial height on the lens and wl is the design wavelength of the diffractive element (synthetic production wavelength).

For the coefficients of the rotationally symmetric component, made to be Fresnel-type, which in this case is present as symmetric component of a diffractive optical element, the following are set:

$g_1$=0.006109 and $g_2$=−4.92E-5.

For the coefficient of the spiral component of the diffractive optical element, the following applies: $k_1$=−0.003. The profile depth of the diffractive optical element is h=0.0043 mm.

In a third example, the intraocular lens 11 with the extended range of focus has the following parameters for a diffractive embodiment of the additional focal power $F_{SS}$, split between the two optical surfaces 2 and 4 of the refractive base lens 3: Corneal radius $R_5$=7.814 mm, aspherical conic constant K=−0.26.

The base radii of the intraocular lens are $R_3$=$R_4$=+/−20.0 mm (spherical). Further parameters are: the distance between corneal radius $R_5$ and optical surface 4 with the radius $R_4$ is 4.12 mm; the central thickness $d_2$=0.65 mm and the distance between the optical surface 2 with the radius $R_3$ and the retina is 18.5 mm; the lens material is "Benz25" and the diameter of the intraocular lens is 6 mm.

In this example, one diffractive optical element has been respectively applied to each of the optical surfaces 2 and 4.

Here, the focal power is split in such a way that the spiral focal power component $F_{spiral}$ lies on the optical surface with the radius $R_4$ and the structure-shaped rotationally symmetric focal power component $F_{structure}$ lies on the radius $R_3$.

With L=2, N=1 and $$w(phi) = \frac{phi}{2\pi},$$

the following emerges:

$$\text{phase}_{SS}(r,\,phi) = g_1 * r^2 + g_2 * r^4 + k_1 * r^2 \frac{phi}{2\pi}$$

and the reduced phase function emerges as $$\text{phase}_{SS\,reduced}(r,\,phi) = \frac{\text{phase}_{SS}(r,\,phi)}{wl} - \text{floor}\frac{\text{phase}_{SS}(r,\,phi)}{wl},$$

where phi=0 . . . 2π (azimuth angle), r=radial height on the lens and wl is the design wavelength of the diffractive element (synthetic production wavelength).

The following applies to the diffractive optical element applied to the optical surface 4:

$g_1$=0 and $g_2$=0 and $k_1$=−0.003.

The profile depth of the diffractive optical element is h=0.0043 mm.

The following applies to the diffractive optical element applied to the optical surface 2:

$g_1$=0.0065 and $g_2$=1.8975E-4 and $k_1$=0.

The profile depth of the diffractive optical element is h=0.0043 mm.

Figure 15:
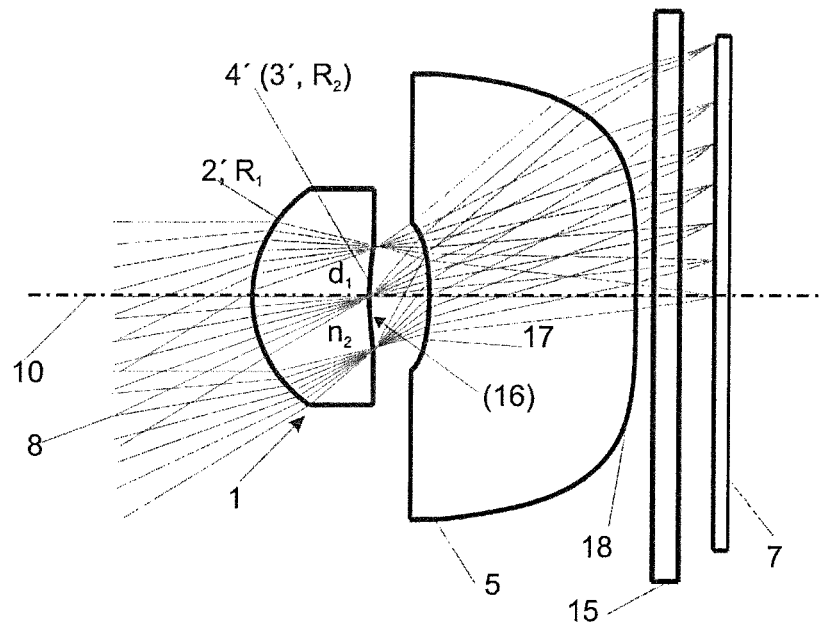
FIG. 15 shows an optical system of a camera with a "thick" lens.

FIG. 15 shows an optical system of a camera in accordance with FIG. 3 from DE 10 2011 101 899 A1 with a "thick" lens 1 which has the extended range of focus. An additional focal power component in the form of a spiral focal power component is added to the base focal power which results from the radii $R_1$, $R_2$, the refractive index $n_2$ and the central thickness $d_1$ of the calculated lens. This spiral focal power component is added to the height profile of the calculated base surface 3' as height profile $z_{spiral}$ and, in practice, is manufactured as second optical surface 4'.

However, the spiral focal power component also can be manufactured on one or both of the optical surfaces of the lens with the base focal power in a diffractive form as diffractive optical element. Alternatively, the spiral focal power component can also be manufactured as refractive index gradient within the lens with the base focal power. Provision is likewise made for arbitrary mixed forms.

Figure 16:
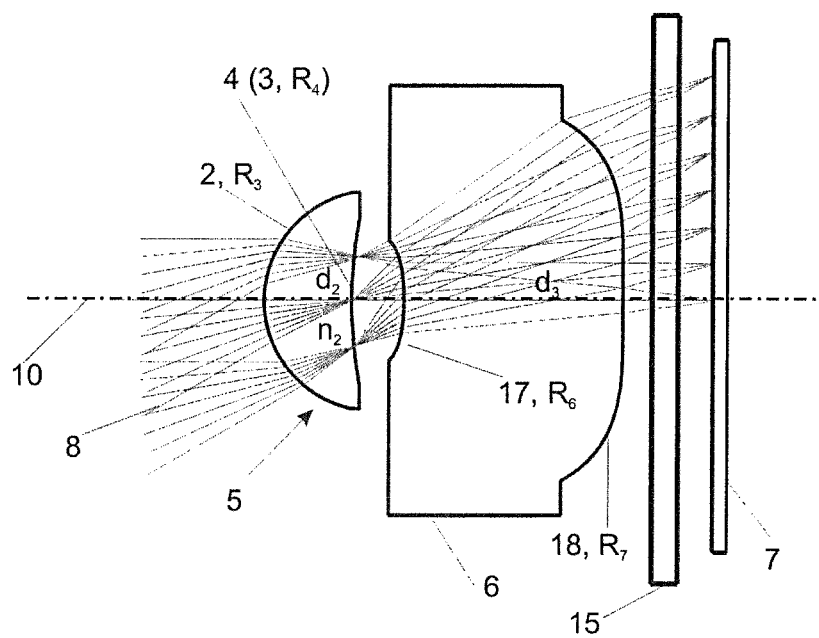
FIG. 16 shows an optical system of a camera with a "thin" lens having the extended range of focus.

FIG. 16 shows an optical system of a camera with a "thin" lens 5 according to the invention which has the extended range of focus. In the example, an additional focal power component in the form of a spiral and Fresnel-shaped height profile $z_{SF}$ is added to the base focal power of the calculated lens. The height profile is added to the height profile of the calculated base surface 3 with the radius $R_4$ and manufactured as second optical surface 4. Also, the spiral and Fresnel-shaped focal power component can be wholly or in part realized by a diffractive optical element on the optical surface of the base lens (or distributed on the two optical surfaces) or by a refractive index gradient in the lens material.

In the light propagation direction, an aspherical lens 6 with the optical surfaces 17 and 18 follows the "thin" lens 5, and the lens is followed by a filter 15 and a sensor 7.

On the object side, the "thin" lens 5 has a first optical surface 2 with the radius $R_3$. Manufactured on the image side is the second optical surface 4, the height profile of which emerges from the height profile $z_{base}$ of the calculated radius $R_4$ and the spiral and Fresnel-shaped height profile $z_{SF}$(r, phi).

A cellular telephone lens system with a focal length of 5.61 mm is shown as an example; it has an installation length of 6.1 mm and an aperture of 1:2.8.

The optical surfaces 2, 17 and 18 of the lenses 5 and 6 have a rotationally aspherical basic form.

Lens 5: lens thickness $d_2$=1.21 mm, material is Zeonex.
Optical surface 2: $R_3$=1.482 mm convex
Asphere coefficients:
K=0.04649
A=−0.698748E-03
B=0.987484E-03
C=−0.119379E-03
D=−0.104254E-02
E=0.323245E-03

The non-manufactured spherical concave base surface 3 has a calculated radius $R_4$=6.303 mm. The spiral and Fresnel-shaped focal power profile in the form of a height profile $z_{SF}$ is added to the height profile $z_{base}$ of this base surface 3. This height profile is then produced on the lens to be manufactured. In this example, the coefficient of the spiral polynomial $c_1$=−0.00268 and the coefficient of the rotationally symmetric Fresnel component $e_1$=0.03.

The additional spiral focal power component is calculated as $$F_{spiral} = 2k_1 * r^2 * \frac{phi}{2\pi}$$

and the additional rotationally symmetric Fresnel component is calculated as $$F_{Fresnel} = 2e_1 * r^2$$

and the overall focal power emerges as $$F_{tot} = F_{base} + F_{SF} = F_{base} + F_{Fresnel} + F_{spiral}$$

$$F_{tot} = F_{base} + 2e_1 * r^2 + 2k_1 * r^2 * \frac{phi}{2\pi}.$$

The additional focal power added onto the base surface 3 is $$F_{SF} = F_{Fresnel} + F_{spiral} = 2e_1 * r^2 + 2k_1 * r^2 * \frac{phi}{2\pi},$$

or, described as a height profile, $$z_{SF} = Z_{Fresnel} + z_{spiral} = 2e_1 * r^2 + 2k_1 * r^2 * \frac{phi}{2\pi}.$$

The indentation depth of the Fresnel grooves is 0.008 mm.
The lens 6 has a thickness of 3.0 mm; the material is polycarbonate.

The optical surface 17 has a radius $R_6 = -3.075$ mm with the following asphere coefficients:
K=11.058298
A=−0.623991E-01
B=−0.926325E-02
C=0.244030E-01
D=−0.125809E+00
E=0.345714E-01
F=−0.101087E-01
G=−0.221418E-15
H=−0.409672E-17
J=0.991703E-20

The optical surface 18 has the radius R7=44.1377 mm (convex) with the following asphere coefficients:
K=−0.238656e57
A=−0.171783E-01
B=0.462293E-03
C=−0.823963E-03
D=0.227317E-03
E=−0.108925E-04
F=−0.474572E-05
G=0.385353E-06
H=0.475909E-07
J=−0.466662E-08

The distance between the lens 5 and the lens 6 is 0.75 mm; the distance between the lens 6 and the filter 15 is 0.4 mm and the distance between the filter 15 and the image plane of the sensor 7 is 0.4 mm, wherein the filter thickness is likewise 0.4 mm.

The lens system supplies a simultaneous range of focus from 330 mm to infinity.

The installation length of the lens system is only 6.1 mm and therefore 0.7 mm less than described in the examples for FIG. 3 in DE 10 2011 101 899 A1.

Here, in particular, the expedient selection of the coefficients c and e in front of the quadratic term supports the achromatization of the lens system.

It is understood that the foregoing description is that of the preferred embodiments of the invention and that various changes and modifications may be made thereto without departing from the spirit and scope of the invention as defined in the appended claims.

REFERENCE CHARACTERS

1 "Thick" lens
2 Manufactured first optical surface (spherical, aspherical, radially symmetric, free-form surface) of a "thin" lens
2' Optical surface of a "thick" lens
3 Calculated base surface of the "thin" lens (spherical, aspherical, radially symmetric, free-form surface)
3' Calculated second optical surface of the "thick" lens
4 Manufactured second optical surface of the "thin" lens (spherical, aspherical, radially symmetric, free-form surface, spiral and structure-shaped surface)
4' Manufactured surface of the "thick" lens
5 "Thin" lens
6 Aspherical lens
7 Sensor
8 Bundle of light
9 Lens edge
10 Optical axis
11 Intraocular lens
12 Cornea
13 Aqueous humor
14 Retina
15 Filter
16 Spiral and structure-shaped diffractive optical element (DOE)
17 Optical surface
18 Optical surface
$F_{tot}(r, phi)$ Overall focal power of the lens
$F_{lens}$ Basic value of the focal power of the base system of a "thick" lens
$F_{base}$ Focal power of the base system of a "thin" lens
$F_{structure}$ Focal power of a structure which is added to the focal power $F_{base}$ of the "thin" lens
$F_{spiral}(r, phi)$ Spiral focal power component which is added to the focal power $F_{base}$ of the "thin" lens
$F_{spiral\ max}(r, phi)$ Maximum focal power of the spiral component of the focal power
$F_{SF}(r, phi)$ Spiral and Fresnel-shaped additional refractive focal power
$F_{SS}(r, phi)$ Spiral and structure-shaped additional focal power
$F_{ss\ diffractive}(r, phi)$ Spiral and structure-shaped additional diffractive focal power
$F_{structure\ diffractive}$ Focal power of the structure in diffractive form
$F_{spiral\ diffractive}(r, phi)$ Spiral focal power in diffractive form
$f_{base}$ Focal length of the base system
$f_{spiral}(r, phi)$ Focal length of the spiral additional focal power
$f_{structure}$ Focal length of the additional focal power of a structure
L, M, N Final values
i, j, l Counters
$c_j, c_1, c_2$ Polynomial coefficients of the spiral for the refractive case $k_j$, $k_1$, $k_2$ Polynomial coefficients of the spiral for the diffractive case
$e_j$, $e_1$, $e_2$ Polynomial coefficients of the component, made to be Fresnel-type, for the refractive case
$g_j$, $g_1$, $g_2$ Polynomial coefficients of the structure-shaped component for the diffractive case
$z_{spiral\ max}(r)$ Maximum height of the spiral (radius-dependent)
$z_{spiral\ max}(r, phi)$ Maximum height (dependent on the radius and the azimuth angle)
$z_{spiral}(r, phi)$ Spiral additive height of the base surface
$z_{base}$ Height profile of the calculated base surface 3
$z_{Fresnel}$ Height profile of the Fresnel structure
$z_{SF}$ Spiral and Fresnel-shaped height profile of the calculated base surface 3
$z_{tot}(r, phi)$ Height profile of the manufactured optical surface 4
$w(phi)$ Angle-dependent component of the focal power profile
$w_i$, $w_1$, $w_2$ Peak positions of the angular distribution function
$a_i$, $a_1$, $a_2$ Damping coefficients for the respective peak positions
$I_i$, $I_1$, $I_2$ Intensity values of the individual peaks
D Lens diameter
r Radius (radial height)
phi Azimuth angle
$R_1$ Radius of the first optical surface of the "thick" lens
$R_2$ Radius of the optical base surface of the "thick" lens
$R_3$ Radius of the first optical surface 2 of the "thin" lens
$R_4$ Radius of the optical base surface 3 of the "thin" lens
$R_5$ Corneal radius
$R_6$ Radius of the aspherical lens
$R_7$ Radius of the aspherical lens
$n_1$ Refractive index of the surrounding medium
$n_2$ Refractive index of the lens material
$d_1$ Central thickness of the "thick" lens
$d_2$ Central thickness of the "thin" lens
$d_3$ Central thickness of the aspherical lens
h Profile depth of the diffractive element
p Indentation depth of the element made to be Fresnel-type
λ Application wavelength
wl Design wavelength of the diffractive element
$phase_{spiral\ max}(r, phi)$ Maximum value of the grating frequency, which corresponds the maximum spiral focal power distribution
$phase_{spiral}(r, phi)$ Phase function of the spiral focal power distribution
$phase_{structure}$ Phase function of the additional structural focal power distribution
$phase_{SS}(r, phi)$ Phase function of the spiral and structure-shaped focal power distribution
t Calculation variable
floor(t) Integer component (floor function)
Profile(r, phi) Phase function reduced to the height h
K Aspherical constant
x, y Cartesian coordinates
$\Delta n_{spiral}$ Spiral refractive index distribution
$\Delta n_{spiral\ max}$ Maximum refractive index of the spiral
$\Delta n_{structure}$ Refractive index distribution of the structure
$\Delta n_{SS}$ Spiral and structure-shaped refractive index distribution

What is claimed is:

1. A lens having an extended range of focus, the lens comprising:
said lens defining an optical axis and being made of a transparent material;
said lens having two finished optical surfaces;
said lens having a focal power distribution ($F_{tot}$); and,
said focal power distribution ($F_{tot}$), in relation to a plane perpendicular to said optical axis, changes as a function of the radial height (r) and of the azimuth angle (phi) between a calculated basic value of the focal power ($F_{lens}$) not equal to zero and a maximum value $F_{spiral\ max}$ (r, phi) so as to cause said focal power distribution ($F_{tot}$) to emerge by calculation as:

$$F_{tot}(r, phi) = F_{lens}(r) + F_{spiral\ max}(r, phi) * w(phi),$$

wherein $F_{spiral\ max}$ (r, phi) depends nonlinearly on the radius and w(phi), which is a factor for the focal power component having the spiral profile, and in that the calculated basic value of said focal power ($F_{lens}$) is split into a refractive focal power component of a base system ($F_{base}$) and into a focal power component of a structure ($F_{structure}$), furthermore a spiral focal power component $$F_{spiral}(r, phi) = F_{spiral\ max}(r, phi) * w(phi)$$

and the focal power component of the structure ($F_{structure}$) being combined to form a spiral and structure-shaped additional focal power $$F_{ss}(r, phi) = F_{structure}(r) + F_{spiral}(r, phi)$$

such that the overall focal power of the finished lens emerges as $$F_{tot}(r, phi) = F_{base}(r) + F_{ss}(r, phi).$$

2. The lens of claim 1, wherein w(phi) is described as a linear profile using the equation $$w(phi) = \frac{phi}{2\pi}.$$

3. The lens of claim 1, wherein the base focal power of the lens ($F_{base}$) and/or the additional focal power of the structure ($F_{structure}$) is/are rotationally symmetric.

4. A lens having an extended range of focus, the lens comprising:
said lens defining an optical axis and being made of a transparent material;
said lens having two finished optical surfaces;
said lens having a focal power distribution ($F_{tot}$); and,
said focal power distribution ($F_{tot}$), in relation to a plane perpendicular to said optical axis, changes as a function of the radial height (r) and of the azimuth angle (phi) between a calculated basic value of the focal power ($F_{lens}$) not equal to zero and a maximum value $F_{spiral\ max}$ (r, phi) so as to cause said focal power distribution ($F_{lens}$) to emerge by calculation as:

$$F_{tot}(r, phi) = F_{lens}(r) + F_{spiral\ max}(r, phi) * w(phi),$$

wherein $F_{spiral\ max}$ (r, phi) depends nonlinearly on the radius and w (phi), which is a factor for the focal power component having the spiral profile, and in that the calculated basic value of said focal power ($F_{lens}$) is split into a refractive focal power component of a base system ($F_{base}$) and into a focal power component of a structure ($F_{structure}$), furthermore a spiral focal power component $$F_{spiral}(r, phi) = F_{spiral\ max}(r, phi) * w(phi)$$

and the focal power component of the structure ($F_{structure}$) being combined to form a spiral and structure-shaped additional focal power $$F_{ss}(r, phi) = F_{structure}(r) + F_{spiral}(r, phi)$$

such that the overall focal power of the finished lens emerges as $$F_{tot}(r, phi) = F_{base}(r) + F_{ss}(r, phi);$$

Wherein w(phi) is described by the equation $$w(phi) = \sum_{i=1}^{M} I_i \exp[-a_i(phi - w_i)^2]$$

and $w_i$ denotes the peak positions of the angular distribution function; $I_i$ denotes intensity values of the individual peaks; $a_i > 0$ denotes damping coefficients for the respective peak positions and i denotes a counter and $M \geq i$ denotes a final value.

5. A lens having an extended range of focus, the lens comprising:
said lens defining an optical axis and being made of a transparent material;
said lens having two finished optical surfaces;
said lens having a focal power distribution ($F_{tot}$); and,
said focal power distribution ($F_{tot}$), in relation to a plane perpendicular to said optical axis, changes as a function of the radial height (r) and of the azimuth angle (phi) between a calculated basic value of the focal power ($F_{lens}$) not equal to zero and a maximum value $F_{spiral\ max}(r, phi)$ so as to cause said focal power distribution ($F_{tot}$) to emerge by calculation as:

$$F_{tot}(r, phi) = F_{lens}(r) + F_{spiral\ max}(r, phi) * w(phi),$$

wherein $F_{spiral\ max}$ (r, phi) depends nonlinearly on the radius and w (phi), which is a factor for the focal power component having the spiral profile, and in that the calculated basic value of said focal power ($F_{lens}$) is split into a refractive focal power component of a base system ($F_{base}$) and into a focal power component of a structure ($F_{structure}$), furthermore a spiral focal power component $$F_{spiral}(r, phi) = F_{spiral\ max}(r, phi) * w(phi)$$

and the focal power component of the structure ($F_{structure}$) being combined to form a spiral and structure-shaped additional focal power $$F_{ss}(r, phi) = F_{structure}(r) + F_{spiral}(r, phi)$$

such that the overall focal power of the finished lens emerges as $$F_{tot}(r, phi) = F_{base}(r) + F_{ss}(r, phi);$$

wherein the spiral and structure-shaped focal power distribution ($F_{ss}$) is created by a height profile, wherein the height profile $z_{tot}$ (r, phi) of the second optical surface to be manufactured emerges from adding a height profile ($z_{base}$) of a calculated base surface, a Fresnel-shaped height profile ($z_{Fresnel}$) of a Fresnel lens and a spiral height profile $z_{spiral}$ (r, phi), wherein the additive height $z_{spiral}$ (r, phi), starting from zero up to a maximum value ($z_{spiral\ max}$) emerges as a function:

$$z_{spiral}(r, phi) = z_{spiral\ max}(r, phi) * w(phi)$$

wherein: the radius (r) changes continuously between 0 and D/2 and the azimuth angle of the aperture (phi) changes continuously between 0 and 2.pi., wherein the spiral height profile $z_{spiral}$ (r, phi) and the Fresnel-shaped height profile ($z_{Fresnel}$) are added to the height profile ($z_{base}$) of the calculated base surface, as result of which the optical surface to be manufactured is described by a spiral and Fresnel-shaped height profile ($z_{FS}$), wherein $$z_{tot}(r, phi) = z_{base} + z_{FS}(r, phi)$$

with $$z_{FS}(r, phi) = z_{Fresnel} + z_{spiral}(r, phi)$$

applies.

6. The lens of claim 5, wherein the forms and/or structures producing the additional spiral and structure-shaped focal power $F_{SS}$ are arranged on one of the optical surfaces of the lens, in each case on their own or combined with one another, and/or also arranged individually or combined with one another and/or in a distributed manner on both optical surfaces of the lens and/or introduced into the material of the lens.

7. The lens of claim 5, wherein the spiral additive height ($z_{spiral}$) emerges from the product of a polynomial for the maximum height $z_{spiral\ max}(r, phi)$, which depends nonlinearly on the radius and the angle, and an angle-dependent component w(phi):

$$z_{spiral}(r, phi) = z_{spiralmax}(r, phi) * w(phi),$$

where $$z_{spiralmax}(r, phi) = \sum_{j=2}^{N} c_j(phi) * r^j$$

or $$z_{spiralmax}(r, phi) = \sum_{j=1}^{N} c_j(phi) * r^{2*j}$$

is the polynomial for the maximum height.

8. The lens of claim 5, wherein the additive height (z) emerges from the product of a polynomial for the maximum height $z_{max}(r)$, which depends nonlinearly on the radius, and an angle-dependent component w(phi):

$$z_{spiral}(r, phi) = z_{spiralmax}(r) * w(phi),$$

where $$z_{spiralmax}(r) = \sum_{j=2}^{N} c_j * r^j$$

or $$z_{spiralmax}(r) = \sum_{j=1}^{N} c_j * r^{2*j}$$

is the radial polynomial for the maximum height.

9. A lens having an extended range of focus, the lens comprising:
said lens defining an optical axis and being made of a transparent material;
said lens having two finished optical surfaces;
said lens having a focal power distribution ($F_{tot}$); and, said focal power distribution ($F_{tot}$), in relation to a plane perpendicular to said optical axis, changes as a function of the radial height (r) and of the azimuth angle (phi) between a calculated basic value of the focal power ($F_{lens}$) not equal to zero and a maximum value $F_{spiral\ max}$(r, phi) so as to cause said focal power distribution ($F_{tot}$) to emerge by calculation as:

$$F_{tot}(r, phi) = F_{lens}(r) + F_{spiral\ max}(r, phi) * w(phi),$$

wherein $F_{spiral\ max}$ (r, phi) depends nonlinearly on the radius and w (phi), which is a factor for the focal power component having the spiral profile, and in that the calculated basic value of said focal power ($F_{lens}$) is split into a refractive focal power component of a base system ($F_{base}$) and into a focal power component of a structure ($F_{structure}$), furthermore a spiral focal power component $$F_{spiral}(r, phi) = F_{spiral\ max}(r, phi) * w(phi)$$

and the focal power component of the structure ($F_{structure}$) being combined to form a spiral and structure-shaped additional focal power $$F_{ss}(r, phi) = F_{structure}(r) + F_{spiral}(r, phi)$$

such that the overall focal power of the finished lens emerges as $$F_{tot}(r, phi) = F_{base}(r) + F_{ss}(r, phi);$$

wherein the focal power distribution is produced by a diffractive optical element, wherein the calculated base surface is manufactured as a second optical surface and the focal power component with the spiral and structure-shaped profile ($F_{ss\ diffractive}$) emerges from the effect of an optical grating, which is applied onto the manufactured second optical surface, furthermore the spiral and structure-shaped additional diffractive focal power ($F_{ss\ diffractive}$) is the sum of the focal power of the spiral in diffractive form ($F_{spiral\ diffractive}$) and the focal power of the structure in diffractive form ($F_{structure\ diffractive}$) and the focal power in phase form is described as $$phase_{ss}(r, phi) = phase_{structure} + phase_{spiral}(r, phi)$$

where the radius (r) changes continuously between 0 and D/2 and the azimuth angle (phi) changes continuously between 0 and $2\pi$, as a result of which the grating manufactured on the optical surface has the spiral and structure-shaped phase profile.

10. The lens of claim 9, wherein the forms and/or structures producing the additional spiral and structure-shaped focal power $F_{SS}$ are arranged on one of the optical surfaces of the lens, in each case on their own or combined with one another, and/or also arranged individually or combined with one another and/or in a distributed manner on both optical surfaces of the lens and/or introduced into the material of the lens.

11. The lens of claim 9, wherein the values for the spiral grating profile are determined by the equation $$phase_{spiral}(r, phi) = phase_{spiralmax}(r, phi) * w(phi)$$

wherein $$phase_{spiralmax}(r, phi) = \sum_{j=2}^{N} k_j(phi) * r^j$$

or $$phase_{spiralmax}(r, phi) = \sum_{j=1}^{N} k_j(phi) * r^{2*j}$$

is the polynomial for the maximum phase value.

12. The lens of claim 9, wherein the values for the spiral grating profile are determined by the equation $$phase_{spiral}(r, phi) = phase_{spiralmax}(r) * w(phi),$$

wherein $$phase_{spiralmax}(r) = \sum_{j=2}^{N} k_j * r^j$$

or $$phase_{spiralmax}(r) = \sum_{j=1}^{N} k_j * r^{2*j}$$

is the radial polynomial for the maximum phase value.

13. The lens of claim 11, wherein the forms and/or structures producing the additional spiral and structure-shaped focal power $F_{SS}$ are arranged on one of the optical surfaces of the lens, in each case on their own or combined with one another, and/or also arranged individually or combined with one another and/or in a distributed manner on both optical surfaces of the lens and/or introduced into the material of the lens.

14. A lens having an extended range of focus, the lens comprising:
said lens defining an optical axis and being made of a transparent material;
said lens having two finished optical surfaces;
said lens having a focal power distribution ($F_{tot}$); and,
said focal power distribution ($F_{tot}$), in relation to a plane perpendicular to said optical axis, changes as a function of the radial height (r) and of the azimuth angle (phi) between a calculated basic value of the focal power ($F_{lens}$) not equal to zero and a maximum value $F_{spiral\ max}$ (r, phi) so as to cause said focal power distribution ($F_{tot}$) to emerge by calculation as:

$$F_{tot}(r, phi) = F_{lens}(r) + F_{spiral\ max}(r, phi) * w(phi),$$

wherein $F_{spiral\ max}$ (r, phi) depends nonlinearly on the radius and w (phi), which is a factor for the focal power component having the spiral profile, and in that the calculated basic value of said focal power ($F_{lens}$) is split into a refractive focal power component of a base system ($F_{base}$) and into a focal power component of a structure ($F_{structure}$), furthermore a spiral focal power component $$F_{spiral}(r, phi) = F_{spiral\ max}(r, phi) * w(phi)$$

and the focal power component of the structure ($F_{structure}$) being combined to form a spiral and structure-shaped additional focal power $$F_{ss}(r, phi) = F_{structure}(r) + F_{spiral}(r, phi)$$

such that the overall focal power of the finished lens emerges as $$F_{tot}(r, phi) = F_{base}(r) + F_{ss}(r, phi);$$

wherein the focal power component with the spiral and structure-shaped profile ($F_{ss}$) emerges from an additive or subtractive refractive index distribution $\Delta n_{ss}$ (r, phi) in the material of the lens, which is a sum of a spiral refractive index distribution $\Delta n_{spiral}$ (r, phi) and a structure-shaped refractive index distribution ($\Delta n_{structure}$):

$$\Delta n_{ss}(r, phi) = \Delta n_{structure} + \Delta n_{spiral}(r, phi)$$

and the refractive index distribution emerges, proceeding from a basic value ($n_2$) up to a maximum value ($\Delta n_{spiral\ max}$), as a function $$\Delta n_{spiral}(r, phi) = \Delta n_{spiral\ max}(r, phi) * w(phi),$$

where the radius (r) changes continuously between 0 and D/2 and the azimuth angle (phi) changes continuously between 0 and 2.pi., as a result of which the spiral and structure-shaped refractive index distribution of the lens material is described for $\Delta n_{ss}$ (r, phi).

15. A lens system defining a beam path and having an extended range of focus, the lens system comprising:

A lens with an extended range of focus arranged as an imaging element in said beam path of said lens system:

said lens defining an optical axis and being made of a transparent material:

said lens having two finished optical surfaces;

said lens having a focal power distribution ($F_{tot}$); and, said focal power distribution ($F_{tot}$), referred to a plane perpendicular to said optical axis, changes as a function of the radial height (r) and of the azimuth angle (phi) between a calculated basic value of the focal power ($F_{lens}$) not equal to zero and a maximum value $F_{spiral\ max}$ (r, phi) so as to cause said focal power distribution ($F_{tot}$) to emerge by calculation as:

$$F_{tot}(r, phi) = F_{lens}(r) + F_{spiral\ max}(r, phi) * w(phi),$$

wherein $F_{spiral\ max}$ (r, phi) depends nonlinearly on the radius and w (phi), which is a factor for the focal power component having the spiral profile, and in that the calculated basic value of said focal power ($F_{lens}$) is split into a refractive focal power component of a base system ($F_{base}$) and into a focal power component of a structure ($F_{structure}$), furthermore a spiral focal power component $$F_{spiral}(r, phi) = F_{spiral\ max}(r, phi) * w(phi)$$

and the focal power component of the structure ($F_{structure}$) being combined to form a spiral and structure-shaped additional focal power $$F_{ss}(r, phi) = F_{structure}(r) + F_{spiral}(r, phi)$$

such that the overall focal power of the finished lens emerges as $$F_{tot}(r, phi) = F_{base}(r) + F_{ss}(r, phi).$$

* * * * *

UNITED STATES PATENT AND TRADEMARK OFFICE
CERTIFICATE OF CORRECTION

PATENT NO. : 9,690,882 B2
APPLICATION NO. : 14/227748
DATED : June 27, 2017
INVENTOR(S) : Hans-Juergen Dobschal It is certified that error appears in the above-identified patent and that said Letters Patent is hereby corrected as shown below:

In Column 3:
Line 5: delete "$F_{tot}$ (r,phi) =$F_{base}$ (r) +$F_{structure}$ (r) +$F_{spiral\,max}$(r,phi)*w" and substitute
-- $F_{tot}$ (r,phi) =$F_{base}$ (r) +$F_{structure}$ (r) +$F_{spiral\,max}$ (r,phi) *w(phi) -- therefor.

In Column 5:
Line 18: delete "$F_{FresnelFresnel}$" and substitute -- $F_{Fresnel}$ -- therefor.
Line 36: insert -- . -- after "$z_{SF}$ (r,phi) =$Z_{Fresnel}$ +$Z_{spiral}$ (r, phi)".

In Column 6:
Line 20: delete "$z_{spiral}$ (r, phi) = $z_{spiral\,max}$ (r) *w(Phi)," and substitute
-- $z_{spiral}$ (r, phi) = $z_{spiral\,max}$ (r) *w(phi), -- therefor.

In Column 12:
Line 36: delete "$z_{tot}(r, Phi) = \left(R_4 = \sqrt{R_4^2 - r^2}\right) + \left[z_{Fresnel}(r) + z_{spiral\,max}(r, phi) * w(phi)\right]$,"

and substitute -- $z_{tot}(r, phi) = \left(R_4 - \sqrt{R_4^2 - r^2}\right) + \left[z_{Fresnel}(r) + z_{spiral\,max}(r, phi) * w(phi)\right]$ -- therefor.

In Column 14:
Line 51: delete "$Phase_{spiral}(r, phi) = Phase_{max}(r) * w(phi) = \sum_{j=1}^{N} k_j * r^{2*j} * w(phi)$,"

and substitute -- $phase_{spiral}(r, phi) = phase_{max}(r) * w(phi) = \sum_{j=1}^{N} k_j * r^{2*j} * w(phi)$. -- therefor.

In Column 20:
Line 55: delete "($F_{lens}$)" and substitute -- ($F_{tot}$) -- therefor.

Signed and Sealed this
Twenty-fourth Day of April, 2018

Andrei Iancu
*Director of the United States Patent and Trademark Office*

CERTIFICATE OF CORRECTION (continued)
U.S. Pat. No. 9,690,882 B2

In Column 21:
Line 63: insert -- , -- after "($z_{spiral\ max}$)".
Line 64: insert -- , -- after "$z_{spiral}$ (r, phi) =$z_{spiral\ max}$ (r, phi) *w (phi)".

In Column 22:
Line 1: delete "2.pi." and substitute -- $2\pi$ -- therefor.
Line 4: insert -- a -- after "as".

In Column 25:
Line 14: delete "2.pi.," and substitute -- $2\pi$, -- therefor.
Line 21: delete "system:" and substitute -- system; -- therefor.
Line 23: delete "material:" and substitute -- material; -- therefor.